United States Patent [19]

Davies

[11] 4,095,603

[45] Jun. 20, 1978

[54] CARDIAC PACER EMPLOYING DISCRETE FREQUENCY CHANGES

[75] Inventor: Gomer L. Davies, Fort Lauderdale, Fla.

[73] Assignee: Cordis Corporation, Miami, Fla.

[21] Appl. No.: 751,259

[22] Filed: Dec. 17, 1976

[51] Int. Cl.² .............................................. A61N 1/36
[52] U.S. Cl. ........................ 128/419 PT; 128/419 PG
[58] Field of Search ....... 128/419 P, 419 PG, 419 PS, 128/419 PT, 419 R, 421, 422, 423

[56] References Cited

U.S. PATENT DOCUMENTS

| | | | |
|---|---|---|---|
| 3,557,796 | 1/1971 | Keller, Jr. et al. ............ | 128/419 PG |
| 3,635,224 | 1/1972 | Berkovits ..................... | 128/419 PG |
| 3,757,793 | 9/1973 | Fester et al. ................... | 128/419 PS |
| 3,841,336 | 10/1974 | Daynard ........................ | 128/419 PT |
| 3,854,472 | 12/1974 | Girot et al. ................. | 128/419 PT X |
| 3,870,050 | 3/1975 | Greatbatch ................... | 128/419 PG |
| 3,903,897 | 9/1975 | Woollons et al. ............. | 128/419 PG |

Primary Examiner—William E. Kamm
Attorney, Agent, or Firm—Kenway & Jenney

[57] ABSTRACT

In the implantable cardiac pacer disclosed herein, a drop in battery voltage is signalled by a discrete change in the stimulation frequency of the pacer. Reliably distinct frequencies are obtained by digitally dividing, by two different integer factors, a stable high frequency pulse signal generated by a mechanically controlled oscillator, for example a piezoelectric crystal controlled oscillator.

12 Claims, 4 Drawing Figures

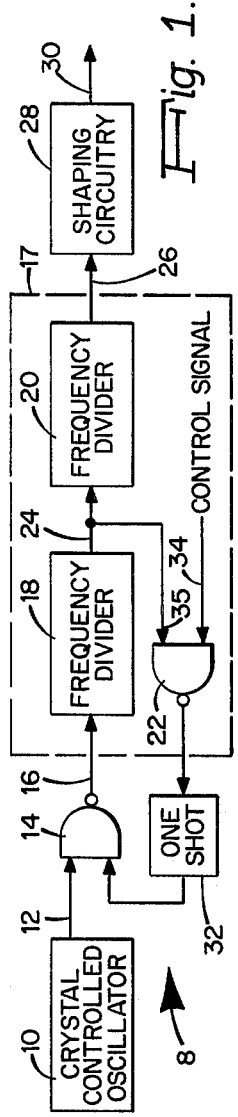
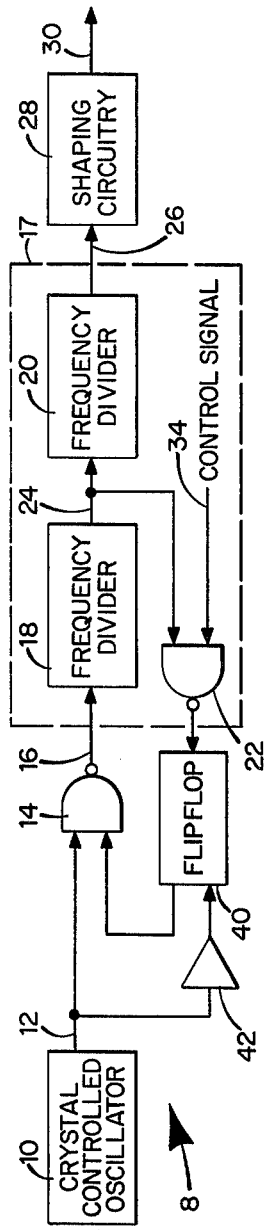
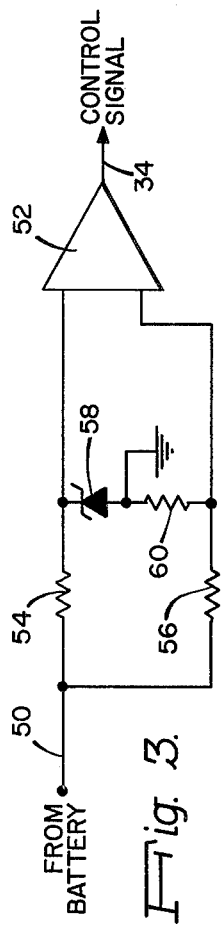
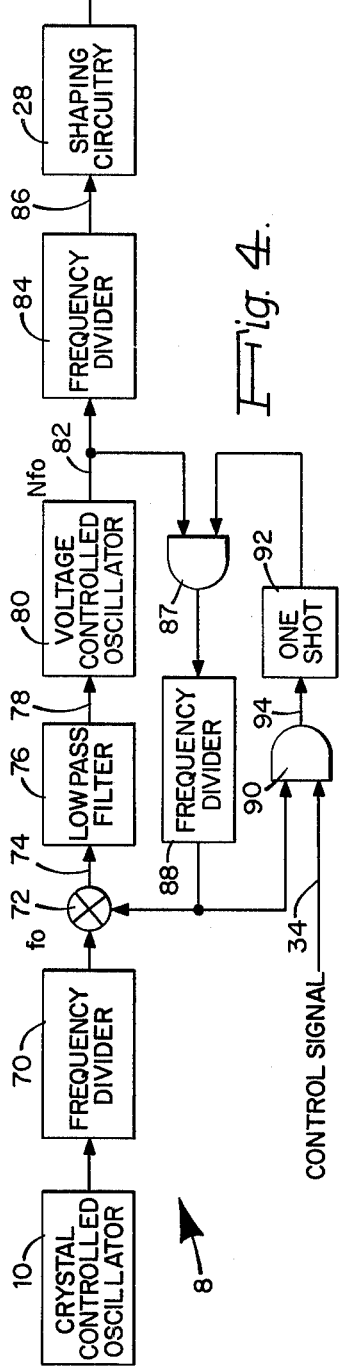

CARDIAC PACER EMPLOYING DISCRETE FREQUENCY CHANGES

This invention relates to fully implanted cardiac pacers and in particular to those pacers using a mechanically controlled oscillator to precisely determine the output pulse rate or frequency.

BACKGROUND OF THE INVENTION

It is now common to fully implant a cardiac pacer within the human body in order to stimulate the heart, either on demand or synchronously, in order to ensure the continued periodic beating of the heart. Such units can often operate for years without need of attention.

In order to increase the reliability of heart pacers, it has been proposed previously to replace the RC oscillator of the older cardiac pacers with a more stable, mechanically controlled oscillator in order to provide a fundamental frequency source whose output frequency is substantially independent of temperature, power supply voltage, external fields, etc. In this connection, digital circuitry, in the form of microcircuits, have been developed and used in order to fully make use of the capabilities and stability of a mechanically controlled oscillator frequency source. In addition, other circuitry has been designed to increase the reliability of the cardiac pacer.

However, there is always the danger, in a fully implanted cardiac pacer, that one or more components will fail or wear out. While it is uncommon for the semiconductor circuit elements to fail in use, other components, such as the battery, have a normal life span of several years or so. While one way of maintaining proper operation of the pacer is to replace the battery periodically, the battery may fail or age prematurely. Thus, it may be vitally important that the condition of the battery or other component be made available or communicated to an outside observer. In this way, premature failure or aging of a component can be detected and the component replaced before the pacer fails to operate properly.

It is therefore a primary object of this invention to provide circuitry whereby a change of state of a condition being monitored is detected and communicated outside of the pacer. Other objects of the invention include the provision of circuitry in a cardiac pacer which is reliable, inexpensive, and simple and which contributes to the reliability of a fully implanted cardiac pacer.

SUMMARY OF THE INVENTION

The invention features a fully implantable cardiac pacer having a cardiac stimulation generator which provides heart stimulation pulses at at least two controlled and well-defined frequencies. The pacer includes at least one component whose operating characteristics or parameter may change. Monitor circuitry responsive to the change of condition of the operating characteristics in at least that one component of the generator provides an output signal which changes in response to predetermined changes in the monitored component. The generator is, in turn, responsive to the output signal and operates at a frequency corresponding to the characteristics of the output signal. A change in the output frequency of the pacer thus signals a change in the condition or operating characteristics or parameters of at least one component of the generator past a predetermined value.

In specific embodiments, the invention features a generator in which the monitor circuitry is responsive to the value of the voltage output of the power source or battery driving the heart pacer. The pacer preferably includes a crystal controlled frequency source or oscillator as its primary or basic frequency standard. The generator includes countdown circuitry for dividing the basic frequency pulse output of the crystal controlled source in order to generate heart stimulation pulses at predetermined frequencies. The countdown circuitry is, in turn, responsive to the monitoring or detection circuitry. The pacer countdown circuitry includes a gating circuitry which is responsive to the monitor circuitry to vary the frequency of the output pulses from the countdown circuitry. In particular, the countdown circuitry has a first state in which the crystal oscillator frequency is divided by a first integer, for example N, and a second state in which the oscillator frequency is divided by a second integer, for example N + d. In general N will be much larger than d. In one preferred embodiment, the countdown circuitry includes at least one binary counter, each counter having a plurality of stages and wherein gating circuitry is connected to feed back the output of at least one of the stages of the counter in combination with the output of the monitor circuitry whereby in one state of the monitor circuitry output at least one output signal from the crystal controlled source to the countdown circuitry is blocked for each generated stimulation pulse.

Other features, advantages and objects will appear from the following description of particular embodiments of the invention taken together with the attached drawings.

BRIEF DESCRIPTION OF THE DRAWINGS

FIG. 1 is a schematic block diagram of one particular embodiment of the invention;

FIG. 2 is a schematic block diagram of a second particular embodiment of the invention;

FIG. 3 is an electrical schematic of monitor circuitry according to the invention for monitoring the condition or operating characteristics of the battery in a cardiac pacer; and FIG. 4 is a schematic block diagram of a third particular embodiment of the invention.

DESCRIPTION OF PARTICULAR EMBODIMENTS

Referring to FIG. 1, the cardiac pacer generally includes a cardiac stimulation generator 8 encased in an appropriate housing (not shown) which is fully implanted in the body. The generator includes a mechanically controlled frequency source 10 which provides the fundamental or standard clock frequency and which, in the preferred embodiment, is a crystal controlled oscillator. A crystal controlled oscillator provides, unlike a typical RC oscillator, a frequency output which is substantially independent of either environmental conditions or battery output voltage. Other mechanically controlled sources, such as a tuning fork or a magnetostriction resonator could be used. The output of crystal oscillator 10 is fed over line 12 to NAND gate 14. The output of the gate 14 over line 16 is delivered to countdown circuitry 17 comprising frequency dividers 18 and 20 and gating circuitry 22 and drives frequency divider 18. Frequency dividers 18, 20 are preferably binary counters having a plurality of stages to reduce by a factor $2^n$ (where $n$ is the number of stages in the respective counters) the frequency of the input source. The output of frequency divider 18, over line 24, is fed, in this embodiment, both to second frequency divider 20 and to gate 22. Gate 22 is shown as a NAND gate. As is well known in the art, frequency dividers 18 and 20 may be combined in any convenient manner so long as the necessary signals are available for use by the remaining portions of the circuitry. The output of frequency divider 20 over line 26 is shaped by a shaping circuitry 28, the output of which is a train of heart stimulation pulses which are then fed to the appropriate location of the heart over line 30.

The output over line 24 which is a periodic train of pulses, is normally blocked or inhibited at gate 22 because the condition or operating characteristic being monitored is in the preset range which defines a normal operating state. In this circumstance, one shot 32 is not initiated or fired and each of the output pulses from crystal controlled oscillator 10 over line 12 passes through NAND gate 14 to frequency divider 18. If, however, the condition being monitored changes, indicating that the operation of the component being monitored could adversely affect operation of the pacer, for example, if the battery voltage were below a predetermined threshold, then, NAND gate 22 is enabled by control signal 34, and the output from frequency divider 18 passes through the NAND gate and initiates one shot 32. The output pulse from one shot 32 is set to have sufficient duration that the next pulse output of crystal controlled oscillator 10 is blocked or inhibited at gate 14. The effect is therefore to require one additional pulse output from crystal controlled oscillator 10 in order to obtain a pulse output from frequency divider 18.

Thus, countdown circuitry 17 effectively divides the frequency of oscillator 10 by one of two integers depending upon which state circuitry 17 is in. In a first state, the circuitry divides the oscillator frequency by a first integer, $N$, and in a second state, by a second integer, $N + d$, $N$ being substantially larger than $d$.

For example, suppose frequency divider 18 is a six stage binary counter, that is, a device requiring $2^6$ or 64 input pulses before an output pulse is delivered over line 24. Then after 64 clock pulses from oscillator 10, frequency divider 18 provides an output pulse over line 24. In this situation, it was assumed that the control signal on line 34 represented a normal condition and one shot 32 is inactive. If, however, the control signal on line 34 indicates an adverse or failure condition, then gate 22 is enabled and an output from one shot 32 will be available to block at least one clock pulse from oscillator 10. In this condition, after frequency divider 18 provides an output pulse over line 24, one shot 32 is fired and gate 14 is disabled for a predetermined period of time. Assuming that only one pulse is blocked, oscillator 10 will provide 65 pulses, of which 64 will reach frequency divider, to produce an output pulse over line 24. As a result, the frequency divider 18 will provide a periodic train of pulses at a slightly lower frequency when the condition being monitored is in an adverse or failure state. In other words, in the normal operating condition or state, the frequency of the output pulse train from frequency divider 18 is the frequency of the oscillator divided by $N=64$ (for the 6 stage binary counter); and in the adverse or failure state, the output frequency of the frequency divider 18 is the frequency of the crystal oscillator divided by $N+d=65$ or approximately 1.5% less.

It is well within the competence of one skilled in digital electronics to change the input 35 to gate 22 to select the output of any one of the binary stages of either frequency divider 18 or 20. The effect is only to vary the percentage frequency change when an adverse condition is detected.

Because of the precise nature of a crystal controlled frequency source, a 1.5% frequency change, while not adverse to the normal operation of the implanted cardiac pacer, will be readily measurable by equipment external to the body and hence a change of the condition being monitored, e.g., low battery voltage, will be made known to an outside observer.

When one shot 32 is undesirable, for example because it is not sufficiently reliable due to the variations in the duration of its output pulse, it can be replaced by a flipflop 40 and inverter gate 42 (FIG. 2). The overall operation of the circuit shown in FIG. 2 is substantially identical to that described with respect to FIG. 1. In normal operation, the output of flipflop 40 does not inhibit pulses from passing through gate 14 to frequency divider 18. After the control signal over line 34 changes, however, indicating a state in which there is an adverse change in the condition of a component, flipflip 40 is set by the next output pulse from frequency divider 18 and upon being set, disables gate 14, thus blocking the next succeeding pulse from crystal controlled oscillator 10 from reaching frequency divider 18. That next pulse does, however, reset flipflop 40 through inverter gate 42. The additional delay introduced by gate 42 is necessary to ensure that flipflop 40 is not reset until after the end of the pulse from the oscillator. Thus, upon the change of state of the signal on line 34, the frequency of the output pulse train from frequency divider 18 is reduced by a small factor. The amount of the reduction depends upon the number of stage in frequency divider 18, or from which stage in the countdown circuitry the input to gate 22 is taken.

In the circuitry described in connection with FIGS. 1 and 2, output of the frequency divider 18, when the condition being monitored is within accepted limits, is the frequency of the oscillator 10 divided by $N=2^n$ where n is the number of binary stages of divider 18. The flipflop of FIG. 2 can introduce a change in the frequency output of the system by requiring one additional oscillator pulse for each frequency divider output pulse, i.e., by dividing the frequency of the crystal oscillator by $N+d=2^n+1$. The one shot circuitry of FIG. 1 has the capability of deleting not only one but any desired number of pulses so that the frequency can be changed by a factor of $N+d=2^n+1, 2^n+2, \ldots$. This capability is limited only by the precision with which one shot 32 can be set.

The control signal 34 indicates, preferably by its voltage level, the condition or state being monitored in a component. The condition can be monitored by any appropriate monitoring or detector circuitry and, referring to FIG. 3, a preferred monitor circuitry for monitoring battery voltage is shown. The voltage from a battery (not shown) over line 50 is delivered to both sides of a voltage comparator 52 through resistive elements 54 and 56. On one side of the comparator the output from the battery through resistive element 54 is dropped across a zener diode 58 to provide a standard for comparison. On the other side of the comparator, the battery voltage is applied to a voltage divider composed of resistive elements 56 and 60. If the battery voltage drops below a predetermined value or level, the voltage at the junction of resistors 56 and 60 drops below the voltage across the zener and the control signal changes value. Thus in this monitor circuitry, the voltage across zener 58 is, over a wide range of input voltages, substantially independent of battery voltage and the voltage at the junction of resistive elements 56 and 60 is proportional to battery voltage to provide the required comparison. Other configurations of monitor circuitry could also be used.

Referring to FIG. 4, there is shown alternative circuitry which provides heart stimulation pulses in which the frequency of the pulses increases upon the change of the control signal 34 from the normal to the adverse or failure state. As in the earlier described circuitry, this circuitry uses a crystal controlled oscillator 10 which feeds a first frequency divider 70 which has the same configuration as divider 18. The output of the frequency divider 70, is fed to a phase detector 72. The output of phase detector 72 over line 74 is a time varying signal indicative of the phase difference between the inputs to the detector. This output is fed to a low pass filter 76 whose output is of the correct level to drive, over line 78, a voltage controlled oscillator 80. The output of the voltage controlled oscillator is available over line 82 and is delivered to a second frequency divider 84. Frequency divider 84 is preferably of the same configuration as frequency divider 20. Its output is delivered over line 86 to the shaping circuitry 28 similar to that shown in FIGS. 1 and 2.

In operation, if the condition being monitored is functioning normally, the output of voltage controlled oscillator 80 is fed through a gate 87 to a frequency divider 88 and thence to phase detector 72. If frequency divider 88 divides the frequency of voltage controlled oscillator 80 by $m=2^n$, (n being the number of binary stages comprising frequency divider 88), then the output of voltage controlled oscillator 80 will stabilize at $mf_o$ ($f_o$ being the frequency of the output pulse train from frequency divider 70) thereby providing a stable operating point for the feedback loop. If the control signal 34 changes state, due to a failure or change of condition of the component being monitored, then gate 90 is enabled and the next output of frequency divider 88 passes through gate 90 and initiates one shot 92 over line 94. The output of one shot 92 is effective to block at least one of the output pulses from voltage controlled oscillator 80. Where one pulse is blocked, the output of frequency divider 88 is then the frequency of the voltage controlled oscillator divided by $m+1$. Thus, in order to provide a stable operating condition for the feedback loop, the frequency output of voltage controlled oscillator 80 must rise to $(m+1)f_o$, thus compensating for the pulse that was blocked by operation of one shot 92. Thus, the output frequency from shaping circuitry 28 will no longer be proportional to $mf_o$ but will become proportional to $(m+1)f_o$.

It should be apparent that the definition of "normal" control signal and adverse or failure control signal is arbitrary. Thus, with respect to the circuitry of FIGS. 1 and 2, the adverse or failure condition could correspond to an output frequency of the frequency of the crystal oscillator divided by $N+d=2^n$ while the normal condition output frequency corresponds to the oscillator frequency divided by $N=2^n+1$. This same reversal also applies to the circuit of FIG. 4 and in each instance is implemented by inverting the control signal level.

The invention has been described in connection with a constant or fixed mode pacer. The invention is equally applicable to a pacer which can be switched from a standby mode to a continuous mode and to a synchronous mode pacer.

It will be readily apparent that a great variety of circuits could be used to implement a discrete frequency change in response to a change in operating condition or parameter such as a low battery voltage. These different circuits would be obvious expedients and would be within the scope and spirit of the invention. Other embodiments will thus occur to those skilled in the art and are within the following claims.

What is claimed is:

1. A fully implantable cardiac pacer comprising
   a cardiac stimulation generator capable of producing stimulation pulses at at least two controlled and well-defined frequencies, said generator including at least one component having an operating condition which can change,
   monitor circuitry responsive to the condition of at least one said component of said pacer to provide an output signal indicative of said condition, said output signal characterized by having a plurality of defined states, and
   said generator having
      clock means for generating primary clock pulses at a frequency higher than the frequency of said stimulation pulses, and
   frequency changing means responsive to said monitor output signal and said primary clock pulses for generating said stimulation pulses at one of said well-defined frequencies depending upon the state of said output signal.

2. The pacer of claim 1 in which said generator includes a battery power source and said monitor circuitry is responsive to the condition of the battery output voltage.

3. The pacer of claim 2 in which said generator clock means includes a crystal controlled frequency source which provides a basic frequency pulse output for said generator.

4. The pacer of claim 3 in which said generator frequency changing means includes countdown circuitry for dividing the basic frequency pulse output of the crystal source to generate said stimulation pulses at a predetermined frequency and said countdown circuitry is responsive to said monitor circuitry output signal to discretely vary the predetermined frequency of the stimulation pulses.

5. The pacer of claim 4 wherein said countdown output signal circuitry includes gating circuitry responsive to said monitor circuitry to enable said variation of the frequency of said stimulation pulses.

6. The pacer of claim 5 wherein said countdown means include at least one binary counter, each said counter having a plurality of stages and wherein said gating circuitry is connected to feed back the output of at least one of said stages in combination with said monitor circuitry output signal to control a count input of said countdown means, and
   said gating circuitry includes means for blocking, in one state of said monitor circuitry output signal, at least one output signal pulse from said crystal source for each stimulation pulse.

7. The pacer of claim 7 wherein said blocking means includes a one shot circuit for generating a pulse signal in response to a signal derived from at least one of said counter stages for blocking said at least one output pulse from said crystal source.

8. The pacer of claim 6 wherein said blocking means includes a flipflop for generating, when said monitor output is in said one state, a blocking signal in response to a set signal derived from at least one of said counter stages and for blocking at least one said output signal from said crystal source said flipflop being further responsive to the other state of said set signal for passing said crystal source output signals.

9. The pacer of claim 3 wherein said generator frequency changing means includes
a voltage controlled oscillator,
phase comparison circuitry for comparing the phase of a signal generated from the output of the crystal source and the phase of a signal generated from said voltage controlled oscillator,
said voltage controlled oscillator having as an input control signal, a signal derived from an output of said phase comparison circuitry,
a feedback path from said voltage controlled oscillator to said comparison circuitry, and
wherein said signal generated from said voltage controlled oscillator is fed in said feedback path from said voltage controlled oscillator to said comparison circuitry, and said feedback path includes circuitry to block, in response to one condition of the output signal of said monitor circuitry, at least one signal pulse output for each stimulation pulse fed back from said voltage controlled oscillator to said comparison circuitry.

10. A fully implantable cardiac pacer comprising:
batteries for powering said pacer;
a crystal controlled oscillator providing a pulse signal of highly stable frequency;
digital countdown circuitry for dividing the frequency of said pulse signal and providing an output signal at reduced frequency, said countdown circuitry having a first state in which said stable frequency is divided by a first integer number and a second state in which said stable frequency is divided by a second integer number;
at least one component characterized by an operating parameter which can change,
a detector responsive to the value of an operating parameter of said pacer for switching said countdown circuitry from one of said states to the other in response to a change in said parameter past a predetermined value; and
circuit means for providing stimulation pulses at a rate determined by the output signal frequency.

11. A fully implantable cardiac pacer comprising:
batteries for powering said pacer;
a crystal controlled oscillator providing a pulse signal of highly stable frequency;
digital countdown circuitry for dividing the frequency of said pulse signal and providing an output signal at reduced frequency, said countdown circuitry having a first state in which said stable frequency is divided by N and a second state in which said stable frequency is divided by $N+d$, where N is substantially larger than d;
a threshold detector responsive to the battery voltage for switching said countdown circuitry from one of said states to the other when the battery voltage drops below a predetermined value; and
circuit means for providing stimulation pulses at a rate determined by the output signal frequency, the rate being thereby indicative of the state of said battery.

12. A fully implantable cardiac pacer comprising
a power source for said pacer,
a cardiac stimulation generator capable of producing stimulation pulses at two controlled and well-defined frequencies,
a monitoring circuit including a threshold detector for providing an output signal having a first and a second state, said first state indicating the power source for said pacer having a voltage output above a predetermined threshold, and said second state for indicating that said power source voltage output is below said predetermined threshold,
the generator including
a crystal controlled frequency source for providing a basic frequency pulse output for the generator,
a first gating circuitry connected to said crystal source,
countdown circuitry for dividing the basic frequency pulse output of the crystal source, said countdown circuitry being connected to said crystal source through said first gating circuitry,
a second gating circuitry connected to at least one stage of said countdown circuitry and to an output of a monitoring circuit, said second gating circuit responsive to said output of the monitoring circuit and operative to disable for a predetermined time said first gating circuit to block at least one pulse derived from said crystal controlled oscillator.

* * * * *

UNITED STATES PATENT AND TRADEMARK OFFICE
CERTIFICATE OF CORRECTION

PATENT NO. : 4,095,603
DATED : June 20, 1978
INVENTOR(S) : Gomer L. Davies

It is certified that error appears in the above-identified patent and that said Letters Patent are hereby corrected as shown below:

In Column 6, claim 7, line 66, after "claim" but before "wherein", "7" should be --6--.

Signed and Sealed this

Twenty-sixth Day of December 1978

[SEAL]

Attest:

RUTH C. MASON
Attesting Officer

DONALD W. BANNER
Commissioner of Patents and Trademarks